United States Patent
Zhou et al.

(10) Patent No.: US 8,529,830 B2
(45) Date of Patent: Sep. 10, 2013

(54) PLASMA STERILIZING-PURIFYING DEVICE AND METHOD FOR AIR STERILIZING AND PURIFYING

(75) Inventors: Yunzheng Zhou, Shanghai (CN); Jianwei Fu, Shanghai (CN); Jin Zhou, Shanghai (CN)

(73) Assignee: Shanghai Tianyun Environmental Protection Technology Co., Ltd., Shanghai (CN)

( * ) Notice: Subject to any disclaimer, the term of this patent is extended or adjusted under 35 U.S.C. 154(b) by 0 days.

(21) Appl. No.: 13/486,228

(22) Filed: Jun. 1, 2012

(65) Prior Publication Data

US 2012/0269677 A1    Oct. 25, 2012

Related U.S. Application Data

(63) Continuation of application No. PCT/CN2010/002082, filed on Dec. 17, 2010.

(30) Foreign Application Priority Data

Dec. 31, 2009  (CN) .......................... 2009 1 0113641

(51) Int. Cl.
*A61L 9/00* (2006.01)
*A62B 7/08* (2006.01)

(52) U.S. Cl.
USPC .............................................. 422/4; 422/121

(58) Field of Classification Search
USPC ....................................................... 422/4, 121
See application file for complete search history.

(56) References Cited

U.S. PATENT DOCUMENTS 7,318,856 B2 *  1/2008  Taylor et al. ...................... 96/16

FOREIGN PATENT DOCUMENTS

| CN | 1833762 | 9/2006 |
|----|---------|--------|
| CN | 101032709 | 9/2007 |
| CN | 101385867 | 3/2009 |
| CN | 101394067 | 3/2009 |
| CN | 201586246 | 9/2010 |
| CN | 201586249 | 9/2010 |
| CN | 201643058 | 11/2010 |
| JP | 2005222779 | 8/2005 |
| WO | 2009/057555 | 5/2009 |

OTHER PUBLICATIONS

International Search Report for international application No. PCT/CN2010/002082, dated Mar. 31, 2011 (6 pages).

* cited by examiner

*Primary Examiner* — Kevin Joyner
(74) *Attorney, Agent, or Firm* — Hamre, Schumann, Mueller & Larson, P.C.

(57) ABSTRACT

The present invention belongs to the technical field of air sterilizing and purification and in particular relates to a plasma air sterilizing and purifying device and an air sterilizing and purifying method. The plasma air sterilizing and purifying device comprises a plasma reactor, a pulse power supply, a fan component, a control device, a power adaptor, and a housing case, wherein the reactor is provided with positive electrodes formed by several nickel-chromium alloy wires or nickel-chromium alloy belts, and the two ends of each positive electrodes are fixed in the corresponding grooves on the micro-discharge preventive conductor rail; and a pulse power supply has a digital control circuit with an oscillator, an error amplifier and a PWM comparator inside which converts signals into a digital control current to control the width of the high-voltage pulse.

8 Claims, 8 Drawing Sheets

PLASMA STERILIZING-PURIFYING DEVICE AND METHOD FOR AIR STERILIZING AND PURIFYING

BACKGROUND OF THE INVENTION

1. Technical Field

The present invention belongs to the technical field of air sterilization and purification and in particular relates to a plasma air sterilizing and purifying device and an air sterilizing and purifying method thereof.

2. Description of Related Art

According to the types of air disinfection factors, the existing air sterilizing and purifying devices are classified into the following six major types: filtering absorption type, electrostatic absorption type, high-energy ion sterilization and purification type, ultraviolet sterilization and purification type, photo-catalytic purification type, and plasma sterilization and purification type; the air sterilizing and purifying method is realized by driving the indoor air to flow through the air sterilizing and purifying device.

The filtering absorption type air sterilizing and purifying device absorbs the suspended particle contaminants and harmful gases in the airflow by means of the Van der Waals' force to realize air purification. This kind of device has the following defects: it exclusively filters dust and cannot perform sterilization; the filtering resistance is increased along with the accumulation of the dust particles, with the dust capacitance reduced and the purification efficiency lowered. The filter screen needs to be cleaned or replaced in time; otherwise, secondary pollution will be caused.

The electronic static absorption type air sterilizing and purifying device separates the particles from the air flow by means of the Coulombic force via the static discharge of an electrode to fulfill the aim of air purification. This kind of device can clear the dust but has a bad sterilization effect and fails to efficiently purify the air and to remove harmful gases such as formaldehyde.

The high-energy ionic sterilizing and purifying device applies a high-frequency electric field onto two electrodes which are isolated by a media to discharge along the plane, and the charges react with the molecules in the air to generate ozone and other substances. This kind of device works by means of the instability and strong oxidation effects of ozone. Ozone is a strong oxidizer which cannot be stored in a site in direct contact with inflammable and explosive gases and cannot gather dust. Once ozone leaks, the respiratory tract of the human body will be injured.

The ultraviolet air sterilizing and purifying device uses a low-pressure mercury vapor discharge lamp to radiate ultraviolet rays with a wavelength of 253.7 nm under the action of high voltage so as to kill microbes such as bacteria and viruses. The ultraviolet rays are invisible light and easily leak and injure the eyes and skin of the human body; the lifespan of the ultraviolet tube is generally less than 8,000 hours. The mentioned defect is one of the reasons that hospitals rarely adopt this kind of device.

The principle of the optical-catalytic purification technology is as follows: under the irradiation of the ultraviolet rays with a wavelength of 387.5 nm, the electrons in the dielectric belt of the photo-catalyst $TiO_2$ are excited to enter the conductive belt to generate corresponding cavities. When the indoor air flows through the surface of the photo-catalyst, the air molecules generate cavities with strong oxidization, namely surface hydroxylation, and the energy is equivalent to a high temperature of 15,000K and can directly kill bacteria and decompose the organic substances into nontoxic and harmless substances such as $CO_2$ and $H_2O$. This technology has the following disadvantages: the optical-catalysis is restrained by the illumination intensity and the air flow, as the inactivation of the $TiO_2$ itself is the fundamental reason for the efficiency decline of the photo-catalytic purification; Furthermore, the ultraviolet rays easily leak and can injure the skin and eyes of the human body.

The existing plasma air sterilizing and purifying device generally consists of a reactor, a high-voltage power supply, a fan component, a control unit, an air inlet, an air outlet, a power adaptor and a housing case; air filters are installed at the air inlet and the air outlet, and the plasma reactor is located in the air flow. The plasma reactor mainly comprises positive electrodes, negative electrodes and a housing case. The positive electrode has several structures, such as metal wires, saw teeth or needle tips. The mechanism of the plasma air sterilizing and purifying device is as follows: The plasma is a gas cloud which consists of a great amount of positive and negative charged particles and neutral particles; it has combined functions of the whole electric field and charges with quasi-neutrality. The plasma can severely break down and damage the cell membranes of bacteria and break the molecular bonds of the gas to generate radicals such as monatomic molecules, negative oxide ions, OH ions, free oxygen atoms and $H_2O_2$, which have strong activation and oxidation capabilities. It has a good effect in killing bacteria and viruses. It also can decompose such macromolecular toxic organics as formaldehyde, benzene, radon, ammonia, carbon monoxide, smoke and TVOC and convert them into nontoxic and scent-free inorganic substances such as carbon and water. The plasma reactor has an electrostatic field which can absorb particles with a minimum particle size of 0.1 um to further purify the air.

Problem to be Solved

The advancement of the plasma air sterilizing and purifying technology has been approved by experts and scholars in this field, and the scientific nature and advancement of its sterilizing and purifying mechanism are incomparable; thus, this technology is internationally accepted as "one of the four technologies of environmental science in the $21^{st}$ century". However, slow progress has been made in its application and promotion in the market. Filtering absorption, high-voltage static and $TiO_2$ photo-catalytic types of air sterilizing and purifying devices are still adopted by hospitals, office buildings, shopping malls and public places of entertainment; the use of ozone and ultraviolet type sterilizing and purifying devices is reduced, but the FFU air filter unit is still widely adopted by the majority of the food factories, pharmaceutical factories and semiconductor IC manufacturers. The FFU air filter unit occupies a large market share even through it has the defects of large energy consumption, high noise and high maintenance cost and the possibility of causing secondary pollution.

One of the fundamental reasons for this problem is unreasonable design of the reactor of the current plasma air sterilizing and purifying device: although the reactor with discharge positive electrode made of thin metal wires generates high-concentration plasma, it is susceptible to burning. Therefore, the discharge positive electrode is usually made of the stainless steel and structured as a saw tooth or needle tip. The saw tooth or needle tip-structured discharge positive electrode is insusceptible to burning, but discharge occurring at the tips forms a discharge column, and a violet and blue light line with a diameter of about 0.2 mm is visible between the positive electrode and the negative electrode in a dark room, which is the phenomenon of non-uniform discharge in the air. The plasma near the violet and blue light line is dense, so the oxygen and nitrogen in the air are susceptible to activation to generate ozone, nitric oxides, etc., while the plasma away from the violet and blue light line is thin, which makes the air sterilizing and purifying effect poor. The sterilizing effect of this kind of reactor is restrained by the concentrations of ozone and the nitric oxides, which is the biggest problem for the technicians in this field. Furthermore, there is another major defect: after working for several months, the saw tooth or the needle tip-structured discharge point becomes blunt because of the sputtering effect. Along with the increasing of the curvature radius of the positive electrode and the rising of the discharge inception voltage, the discharge current is reduced, and then the air sterilizing and purifying efficiency is certainly lowered. This decline phenomenon is invisible, and it is difficult to find the reduction of the plasma concentration; although the reactor surface still works, it is almost ineffective. If this kind of device is used in operating rooms and intensive care units of hospitals, unqualified sterilization may generate bacteria and viruses and cause infection and operation failure.

For example, the Chinese patent "Building Block-type Narrow-spacing Electrostatic Field Device" with application No. 200710038821.4 indicates that "the defect that the thin wire is easy to break greatly lowers the reliability of the device" in the first page of its description. The technical scheme of this invention provides a building block-type narrow-spacing electrostatic field device, comprising a discharge electrode (positive electrode), a dust collector (negative electrode) and an insulator, wherein the discharge electrode and the dust collector are arrayed in parallel at an interval, the two ends of the discharge electrode are connected with discharge electrode connections, the lower part of the discharge electrode is saw tooth-like, the upper part of the discharge electrode is tubular, the saw tooth-like discharge electrode end and the dust collector form a dust collection region; the two ends of the dust collector are connected with dust collection connections; and the discharge electrode connections and the dust collection connections are connected with the insulator, respectively.

The Chinese patent-ionization Type Air Purifier with application No. 200610024299.X has the following statement in the claims: An ionization-type air purifier consists of several positive electrodes and negative electrodes which are identical in length and fixed on insulation boards respectively to form a rectangular electric field, the positive electrodes are arrayed in rows and the two ends thereof are vertically fixed on the insulation boards. Due to the micro-discharge effect generated between the positive electrodes and the insulation boards, the metal wires forming the positive electrodes are burned out after just a few months.

Another reason is that the currently used power supply does not match with the plasma reactor with a capacitive load. The experiments show that to make the reactor generate high-concentration plasma by means of corona discharge at atmospheric pressure to improve the sterilizing and purifying effect, two conditions must be met. First, the external high-voltage electric field only applies energy to the electrons in the air to realize a transient temperature rise (order of nS) and acceleration; electrons with small mass obtain kinetic energies and their temperatures are increased to dozens of thousands of degrees centigrade, while other particles only obtain little energy. Another condition is that the time (order of µS grade) that the external electric field costs to apply the energy to the electrons shall be far shorter than the time cost not to apply energy to the electrons, so the energy obtained by the gas can be transmitted outside in time to avoid efficiency reduction because of excessively heated plasma. The plasma power supply thereof is required to provide a direct-current high voltage in a scope of 10-20 KV and have a high-frequency, narrow-pulse current with a high duty ratio and a rise rate of at least an order 120 nS. Meanwhile, considering that the plasma reactor is a capacitive load, short circuits are inevitable after the positive and negative electrodes work for a long time, which puts forward strict requirements for the safety and stability of the plasma power supply. The switch-on and switch-off time of the semiconductor power switch is of an order of µS, so it is difficult to meet the regular design scheme for the two conditions. The nS-order high-voltage resistant power switch is very expensive, has a short service life and is impractical to apply to civil products.

Thus, simple and low-cost direct-current high-voltage power supplies are the major options in the market. It is known that the plasma formed by the corona discharge of the direct current has a small activity space which is restrained to be near the corona discharge. If the voltage of the direct current is higher than the critical values of the positive and negative electrodes of the reactor, the gas will be broken down to form spark discharge; then, the gas temperature rises, efficiency declines and energy consumption increases, and a great amount of ozone will be generated. For example, the technical scheme of the high-voltage alternating current rectification filter adopts the direct-current high-voltage power supply. Some manufacturers directly adopt a piezoelectric ceramic transformer which outputs a high-frequency alternating current of several thousand, volts, and then the voltage-multiplying rectification filter circuit must be used to make the voltage rise to meet the corona discharge requirements, which is also the high-voltage direct current that is output. If the mentioned power supply is adopted, the plasma reactor with the capacitive load will inevitably have the phenomena of sparking and arc discharge and generate ozone.

The direct-current and alternating-current combined power supply used for the plasma reactor by many manufacturers in the world is realized by applying a high-frequency high-voltage alternating current on the basis of the high-voltage direct current. The combined power supply has a lower peak voltage of corona discharge and a wider voltage scope in comparison with the direct current power supply but is inferior to the narrow-pulse corona discharge, so the quantity and activity space of the active particles fall in between the direct current corona discharge and the narrow-pulse corona discharge. As a power supply of the plasma reactor, it is undesirable.

In the prior art, the root cause of the thin metal wires forming the positive electrode of the plasma reactor easily burning out is the micro-discharge effect which is not found; the physical factors are also unclear, and thus the technical scheme for preventing the micro-discharge effect cannot be figured out. The majority of the manufacturers now producing air sterilizing and purifying devices which have a plasma reactor with a saw tooth or needle tip-structured positive electrode adopt the metal wire as the positive electrode of the plasma reactor. Because of "breakage of the metal wire', those manufacturers have to turn to production of the electrostatic absorption type or plasma type air sterilizing and purifying device with needle tip or saw tooth-structured electrodes, exchanging the sterilizing and purifying effect for the reliability and service life of the sterilizing and purifying device. The technical scheme of replacing the metal wire by the saw tooth or needle tip-structured discharge electrode is a kind of bias. Furthermore, due to unmatched high-voltage direct current power supply, the current plasma air sterilizing and purifying device has low reliability, a short service life and a low air sterilizing and purifying effect, so the application and promotion of the plasma air sterilizing and purifying device is restrained.

BRIEF SUMMARY OF THE INVENTION

One object of the present invention is to overcome the mentioned defects and bias of the prior art and provide a plasma air sterilizing and purifying device which has high reliability and a long service life, generates high-concentration plasma and improves the air sterilizing and purifying efficiency.

Another object of the present invention is to provide an air sterilizing and purifying method for solving the mentioned problem.

The key to designing the plasma air sterilizing and purifying device is the use of two core units, namely the reactor and the matched high-voltage pulse power supply. The experiments of the optimal scheme prove that the saw tooth or needle tip-structured discharge electrode of the reactor of the plasma air sterilizing and purifying device performs static discharge at the tip, while the electrode made of the nickel-chromium alloy wires or nickel-chromium alloy belts performs corona discharge along its four sides. The uniformity and strength of the plasma generated by the positive electrode made of the nickel-chromium alloy wires or nickel-chromium alloy belts under the same conditions are better, and thus the present invention uses the positive electrode made of the nickel-chromium alloy wires or nickel-chromium alloy belts as an example.

Research and analysis show that to solve the problem of insulation between the positive and negative electrodes of the plasma reactor, the majority of the technicians at present directly use supports made from insulation materials to fix the alloy wire positive electrode of the plasma reactor. Studies show that insulation materials with a high dielectric constant can isolate the high-potential positive and negative electrodes well but have a fatal defect that the micro-discharge phenomenon appears in the plasma reactor; Furthermore, along with the increase of the working time, the atmosphere humidity and stacked dust on the surface of the electrode cause leakage and creepage. The higher the dielectric constant is, the more severe the surface micro-discharge phenomenon is. To improve the sterilizing and purifying effects, the voltage of the external power supply of the plasma reactor is usually enhanced to form a strong electric field around the positive electrode, and then the micro-discharge appears in the local area of the metal wire contacting the insulation materials under the catalysis action of the plasma. The high-energy electrons generated by the micro-discharge phenomenon directly ionize and decompose the molecules of the insulation materials and the metal conductive materials to generate oxides and water. This is the root cause of the thin metal-wire discharge positive electrode of the plasma reactor being easy to burn out.

The inventor used the high-voltage pulse power supplies with the same specifications to make contrast tests on the non-thermal plasma reactors with wire, saw-tooth and needle tip-structured positive electrodes by continuous electrification in a closed environment. The working currents of reactors with the saw-tooth and needle tip-structured positive electrodes declined obviously only after the reactors worked for two weeks, and the reactor with the wire-structured positive electrode had wires broken after working for 6 weeks. The bottoms of all the reactors were covered by a dark liquid; the surfaces of the insulators between the positive and negative electrodes had traces of yellow and dark creepage, and the surface of the positive electrode in this area was also corroded. The reactor with a thin spring between the insulation support and the metal wire had similar problem, and the wire breakdown was just delayed by about two or three months. This is because the spring is not allowed to be thick; otherwise, the metal wire is easy to break down by pulling or the spring does not work. Even springs made of the stainless steel are inevitably corroded by the micro-discharge.

When the aging experimental device of the mentioned plasma reactor is influenced by the micro-discharge which is generated by means of the interaction between the metal and the insulation material surface of the electrode support, the density of a small part of the plasma is reduced because of the pollution caused by the micro-discharge, which further reduces the efficiency of the reactor, damages the structure of the reactor and shortens the service life. Therefore, a practical and feasible technical scheme is provided on the basis of study and analysis of the micro-discharge mechanism.

The technical scheme of the present invention is as follows:

The plasma air sterilizing and purifying device comprises a plasma reactor, a pulse power supply, a fan component, a control unit, an air inlet, an air outlet, a power adaptor and a housing case. Air filters are installed at the air inlet and the air outlet, and the plasma reactor is located in the air flow. The plasma reactor has positive electrodes made of several nickel-chromium alloy wires or nickel-chromium alloy belts arrayed in parallel at an equal interval on the same plane, and the positive electrode is positioned at the middle of two adjacent negative electrodes; the two ends of the positive electrode are fixed on a micro-discharge preventive conductor rail, and the two ends of the micro-discharge preventive conductor rail are fixedly and electrically connected with four positive electrode metal supports at the four sides of the reactor; each upper and lower end of each positive electrode metal support are respectively provided with an insulation connection fixed in the mounting hole corresponding to the reactor housing; and the upper and lower ends of the negative electrodes are directly fixed on and electrically connected with the metal reactor housing. An EMC filter, a rectifier circuit, a filter circuit, a digital control circuit, a pulse generator and a pulse transformer are installed in the pulse power supply for the plasma reactor and electrically connected in turn, and the output end of the pulse transformer is externally connected with the plasma reactor; the output end of the pulse generator is provided with a current detecting circuit to send the detected current signals output from the pulse generator into an oscillator, an error amplifier and a PWM comparator in the digital control circuit, and the signals are converted into the digital control current and then output into the input end of the pulse generator; the primary coil and the secondary coil of the pulse transformer have dotted terminals a1 and a2 and unlike terminals b1 and b2 disposed reversely; the secondary coil is formed by two wound segments connected in series, and the upper end of each coil is respectively provided with a high-voltage fast-recovery diode. A semiconductor switching tube Q1 is installed in the pulse generator, the drain electrode is connected with the dotted terminal a1 of the primary coil, the grid electrode is connected with the output end of the integrated circuit IC1 in the digital control circuit via a resistor R4, and the source electrode is connected with a resistor R5 in the current detecting circuit.

Preferably, the present invention has a second technical scheme for the plasma air sterilizing and purifying device: the micro-discharge preventive conductor rail is made of an aluminum bar or a stainless steel bar, and the two ends of the positive electrode made of several nickel-chromium alloy wires or nickel-chromium alloy belts are fixed and located in grooves at the corresponding positions on the micro-discharge preventive conductor rail.

Preferably, the present invention has a third technical scheme for the plasma air sterilizing and purifying device: the pulse transformer is provided with a multi-groove insulation coil frame, and the secondary coil is formed by three to five wound segments connected in series in the corresponding grooves of the multi-groove insulation coil frame; iron-based ultra-crystalline cores for electromagnetic coupling are located in the inner holes of the primary coil and the secondary coil, and the magnetic loops of the iron-based ultra-crystalline cores have magnetic air gaps.

Preferably, the present invention has a fourth technical scheme for the plasma air sterilizing and purifying device: the fan component is provided with a low-noise fan having blades with saw tooth-shaped edges.

Preferably, the present invention has a fifth technical scheme for the plasma air sterilizing and purifying device: the control unit has an air quality sensor and a single-chip controller, the output end of the air quality sensor is connected with the input end of the single-chip controller electrically, and the output end of the control unit is connected with the switches of the pulse power supply and the fan component electrically.

Preferably, the present invention has a sixth technical scheme for the plasma air sterilizing and purifying device: the output ground potential end of the pulse transformer is connected with an abnormal state protective circuit, the output end of the abnormal state protective circuit is connected with the input end of the digital control circuit to sample the working current sent from the pulse transformer to the plasma reactor, the signal current undergoing the photoelectric isolation is sent to the input end of the digital control circuit, and the control current undergoing digital treatment from the output end of the digital control circuit is sent to the input end of the pulse generator, so the width of the output pulse is controlled automatically; and the two ends of the primary coil of the pulse transformer are provided with pulse amplitude-limiting circuits to perform clamping on the peak values of the voltage output from the two ends of the primary coil of the pulse transformer.

Preferably, the present invention has a seventh technical scheme for the plasma air sterilizing and purifying device: the EMC filter is provided with a differential-mode inductor L1 and a common-mode inductor L2 which are connected in series, and the input end and output end of the EMC filter are respectively connected with a capacitor in parallel.

The present invention provides an air sterilizing and purifying method for the plasma air sterilizing and purifying device: the indoor air flows through the plasma air sterilizing and purifying device which has a reactor with a micro-discharge preventive conductor rail and a pulse power supply matched with the power supply. According to the present invention, the pulse frequency is 38 $KH_Z$, the pulse width is 5 $\mu S$, the pulse rise time is 80 nS, the pulse amplitude is 16 $KV_{P-P}$, and the disinfection factors are non-thermal plasma. The air sterilizing and purifying method comprises the following four steps:

A. At atmospheric pressure, the indoor air is forced to flow through the plasma air sterilizing and purifying device at a speed of 0.3-0.6 m/s; by means of corona discharge the plasma air sterilizing and purifying device generates non-thermal plasma with electrons whose temperature is up to tens of thousands of degrees centigrade, so microbes such as bacteria and viruses are unable to survive in this environment; the cells of the microbes such as bacteria and viruses are non-elastically collided by the high-energy electrons, the microbe particles bring a certain amount of charge in the electric field generated by the plasma, and static electricity generated on the surfaces of the microbe particles breaks up the cell membranes and causes cytoplasm to flow out, thus creating another way to kill the microbes;

B. When the high-energy electrons of the plasma are collided with the molecules in the air, a series of elementary reactors occur to generate various active radicals and active oxygen, such as OH, O, $H_2O$, $H_2O_2$ and $O_3$, which can decompose many kinds of organic macromolecular particular smells and reduce them into harmless micro-molecular inorganic substances;

C. Fine particle contaminants with a particle size of 0.1-5 $\mu m$ in the indoor air are effectively gathered by means of the condensation between the ions in the plasma and the fine particles, while fine particle contaminants with a particle size of 5-10 $\mu m$ are removed by the air filter installed in the plasma air sterilizing and purifying device;

D. The flow of the indoor air passing through the plasma air sterilizing and purifying device per hour is at least 10 times the indoor air volume.

Compared with the prior art, the present invention has the following advantages:

In the plasma air sterilizing and purifying device, the positive electrode of the plasma reactor is made of several nickel-chromium alloy wires or nickel-chromium alloy belts fixed on the micro-discharge preventive conductor rail, away from the insulation connection; the two ends of the micro-discharge preventive conductor rail are fixed and electrically connected with four positive electrode metal supports which are installed on the four sides of the reactor orthogonally. Because only one end face of the insulation connection contacts the surface of the micro-discharge preventive conductor rail, so compared with the prior art, the micro-discharge effect thereof is basically negligible. It should be particularly specified that because the cross section of the micro-discharge preventive conductor rail is bigger than those of the nickel-chromium alloy wires or nickel-chromium alloy belts, even if there is a weak micro-discharge effect, the normal work and service life of the plasma reactor are not affected. Thus, each nickel-chromium alloy wire or nickel-chromium alloy belt performs corona discharge stably in the strong direct current dielectric field to generate high-concentration plasma. The defect that "the thin wire is easy to break" is overcome, and the technical bias of "scarifying the sterilizing and purifying effect to obtain reliability and service life of the sterilizing and purifying device by replacing the positive electrode made of the thin metal wire by the saw-tooth or needle tip-structured discharge positive electrode" is corrected. Furthermore, because the lead of the negative electrode of the external direct current power supply is connected with the ground wire of the housing of the plasma reactor, the electromagnetic shielding effect is better and meets the requirements for electromagnetic comparability.

The upper and lower ends of each positive electrode metal support are respectively provided with an insulation connection fixed in the corresponding mounting holes on the housing, and the upper and lower ends of the negative electrodes are fixed on and electrically connected with the inner wall of the housing. And thus, the positive electrode formed by the several nickel-chromium alloy wires or nickel-chromium alloy belts, the micro-discharge preventive conductor rail, the four positive electrode metal supports and the housing of the plasma reactor are tightly integrated together and have high insulation. The upper and lower sides of the negative electrodes are also fixed on the housing to ensure that the positive electrodes are positioned at the middle between two adjacent negative electrodes with high precision during integrated installation to make the discharge uniform, which is a key indicator for measuring the plasma reactor; moreover, such design makes the whole structure of the plasma reactor solid.

In the pulse power supply of the present invention, the output end of the pulse generator is provided with a current detecting circuit, and the detected current signal output from the generator is sent to the oscillator, error amplifier and PWM comparator in the digital control circuit, converted into the digital control current and then output to the input end of the pulse generator, so that the width of the pulse output from the pulse generator is adjusted automatically. The current detection circuit is well matched with the digital control circuit to obtain a high-frequency, narrow-pulse drive current, so the capacitive plasma reactor generates the high-concentration plasma; then, the discharge current is stable during work. The dotted terminals a1 and a2 and the unlike terminals b1 and b2 of the primary coil and the secondary coil of the pulse generator are located transversely, and the pulse generator and the pulse transformer are installed in accordance with a flyback inverter; the secondary coil is formed by at least two wound segments connected in series, and the upper end of each segment is provided with a high-voltage, fast-recovery diode of which the anode is pressed against the tail end of the low-potential segment and the cathode is connected with the starting end of the high-potential segment. By means of such design, the distributed capacitance of the primary coil and secondary coil of the pulse transformer is reduced exponentially according to the wound segments to greatly improve the rise and decline rate of the output pulse voltage. Because the output pulse voltage is relatively stable, so accidents such as sparking are avoided in the capacitive plasma reactor. It must be specified in the design that: the pulse generator and the pulse transformer installed in accordance with the flyback inverter play the role of isolating the plasma reactor connected with the pulse generator and pulse transformer from the mains supply except for enhancing the voltage, and the housing can be directly grounded and has a good electromagnetic shielding effect and high safety.

Meanwhile, the following unexpected beneficial effects are obtained: the expensive, ultra-high speed, large-power switch with a short service life can be replaced by the common high-countervoltage power transistor; even if the plasma reactor is short-circuited due to an accident, the pulse power supply in the present invention is not damaged without the abnormal state protective circuit. This is because the pulse current output by the flyback inverter is a high-voltage corona discharge current with a pulse rise time of below 80 nS obtained by releasing the magnetic energy stored by the pulse generator at the moment of shutdown in the primary coil of the pulse transformer; when the plasma reactor is short-circuited due to an accident, the secondary coil of the pulse transformer is switched on and output by the isolation action of the flyback inverter at the moment of the shutdown of the pulse generator, so the semiconductor tube of the switch of the pulse power supply works safely.

All units of the present invention are coordinated with one another and connected integrally, so the pulse power supply designed in the present invention can be matched with the capacitive plasma reactor and generate the output pulse at a frequency of 20-100 $KH_Z$ during work, wherein when the duty ratio is 20%, the pulse width is 10-2 μS, the pulse rise time is 70-120 nS, the pulse amplitude is 12-18 $KV_{P-P}$, and the disinfection factors are high-concentration non-thermal plasma.

The pulse power supply for the plasma reactor also has the following three advantages:

First, the positive electrode of the reactor is wire or belt-structured, so the corona discharge is uniform; the pulse power supply has a high narrow-pulse voltage, is insusceptible to sparking discharge, and can provide several orders of magnitude more active particles than those provided by the direct current discharge method;

Second, in electric fields where the front edge of the narrow pulse rises quickly, the plasma reactor has a big inner corona area, the electron density of the discharge space is increased, the spatial charge effect distributed in the reactor becomes uniform, and thus the active space is made much bigger than that provided by the direct and alternating current combined power supply.

By means of the two mentioned advantages, because the electrons in the plasma reactor provided by the present invention are dense and widely distributed, there is a large room for the reactor design; therefore, a certain error is allowed during manufacturing, and the qualification rate is high.

All in all, the present invention has the advantages of generating high-concentration plasma and improving the air sterilizing and purifying efficiency while maintaining high reliability and long service life. The circuit of the present invention has a simple design, complete functionalities, an ingenious structure and low cost and is well matched with the plasma reactor.

The plasma reactor and the pulse power supply are two key parts of the plasma air sterilizing and purifying device of the present invention, the anode of the output end of the pulse power supply is electrically connected with the positive electrode of the plasma reactor, the cathode of the output end of the pulse power supply is electrically connected with the negative electrode of the plasma reactor, and the plasma reactor positioned between the air inlet and air outlet of the air sterilizing and purifying device and externally connected with a fan component and can sterilize and purify the air under the control of the control unit. The plasma air sterilizing and purifying device has a broad-spectrum sterilization effect on the following bacteria and viruses: *staphylococcus aureus, colibacillus, bacillus subtilis, candida albicans*, mould, mycoplasma, hepatitis B and flu. Meanwhile, it also has the functions of removing dust, blood smells and particular smells and degrading formaldehyde, smog and organic waste gases such as TVOC. The invention provides an air sterilizing and purifying method for the plasma air sterilizing and purifying device, wherein the pulse power supply outputs pulses at a frequency of 38 $KH_Z$, the pulse width is 5 μS, the pulse rise time is 80 nS, the pulse amplitude is 16 $KV_{P-P}$, and the disinfection factors are the non-thermal plasma. By four steps, bacteria, viruses, many kinds of organic macromolecular particular smells and thin particle contaminants in indoor air can be removed. Experiments showed that: when applied to sterilize and purify a 20 $m^2$ closed room with *staphylococcus albus* sprayed beforehand, the average bacteria killing rate was 99.98% after 30 min and 100% after 60 min, the formaldehyde degradation rate was 98.7%, the quantity of the suspended particles was less than or equal to 3,500/L, (Φ≧0.5 μm), and ozone residing in air was less than or equal to 0.05 mg/$m^3$.

The energy conservation is conspicuous: the power consumed by the reactor which meets the type-II hospital environmental sterilization standards when working in a 100 $m^3$ room is 7-8 W, while the ultraviolet or ozone type air sterilizing and purifying device at least consumes 160 W of power to achieve the same effect.

Descriptions of the Signs of Major Parts in the Attached Drawings

1—plasma reactor
2—pulse power supply
3—fan component
4—control unit
5—air inlet
6—air outlet
7—power adaptor
8—housing
9,10—air filter
101—positive electrode
102—negative electrode
103—micro-discharge preventive conductor rail
104—metal support for positive electrode
105—insulation connection
106—fixing bolt for insulation connection
107—fixing ring for conductor rail
108—reactor housing
109—polluted air at the air inlet
110—clean air at the air outlet
201—EMC filter
202—rectifier circuit
203—filter circuit
204—digital control circuit
205—pulse generator
206—pulse transformer
207—plasma reactor
208—current detection circuit
209—abnormal state protective circuit
210—pulse amplitude-limiting circuit
211—primary insulation coil frame
212—multi-groove insulation coil frame
213—high-voltage lead
214—primary coil
215—secondary coil
216—iron-based ultra-crystalline core
217—high-voltage fast-recovery diode
218—magnetic air gap

DETAILED DESCRIPTION OF THE INVENTION

Embodiment 1

Figure 1:
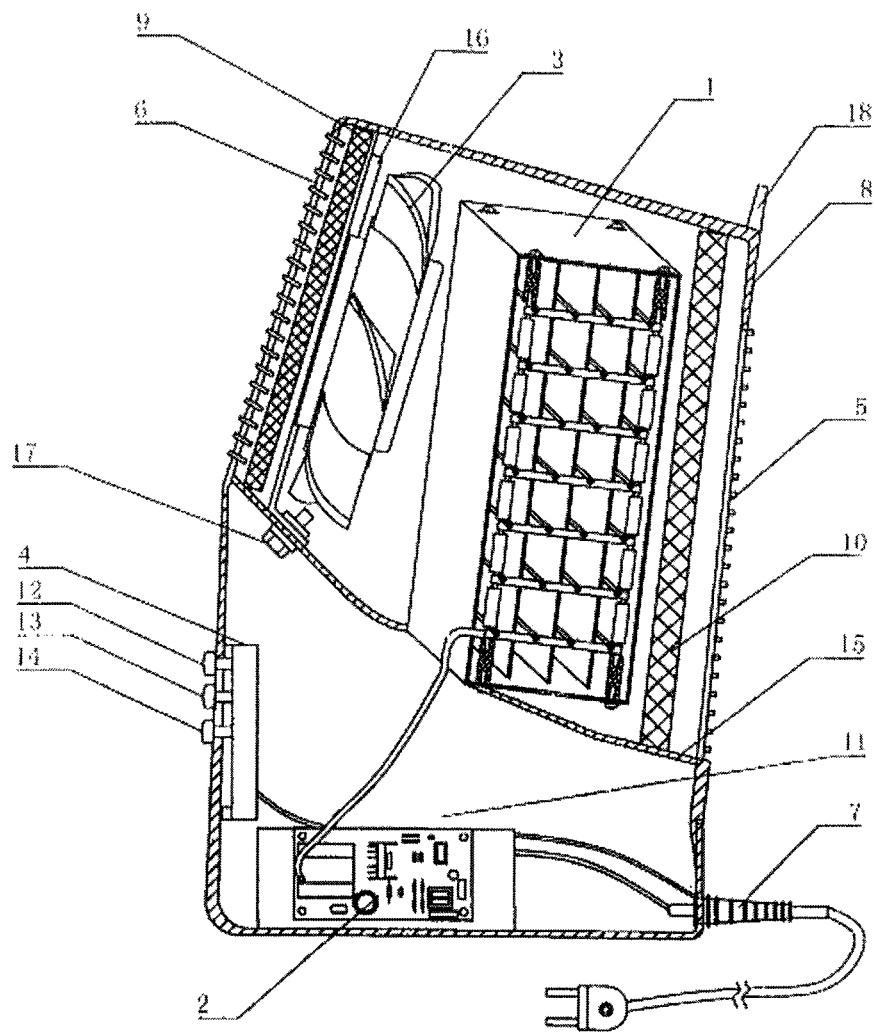
FIG. 1 is a structural view of a plasma air sterilizing and purifying device provided by the present invention.
Figure 2:
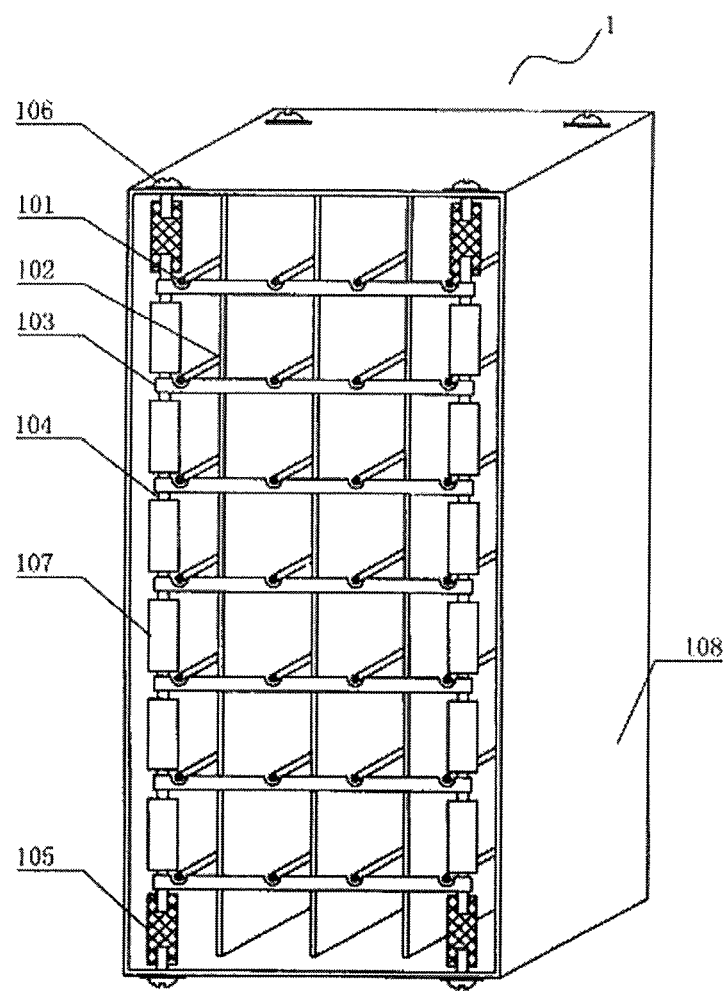
FIG. 2 is a three-dimensional view of a plasma reactor with a positive electrode made of nickel-chromium alloy wires provided by the present invention.
Figure 3:
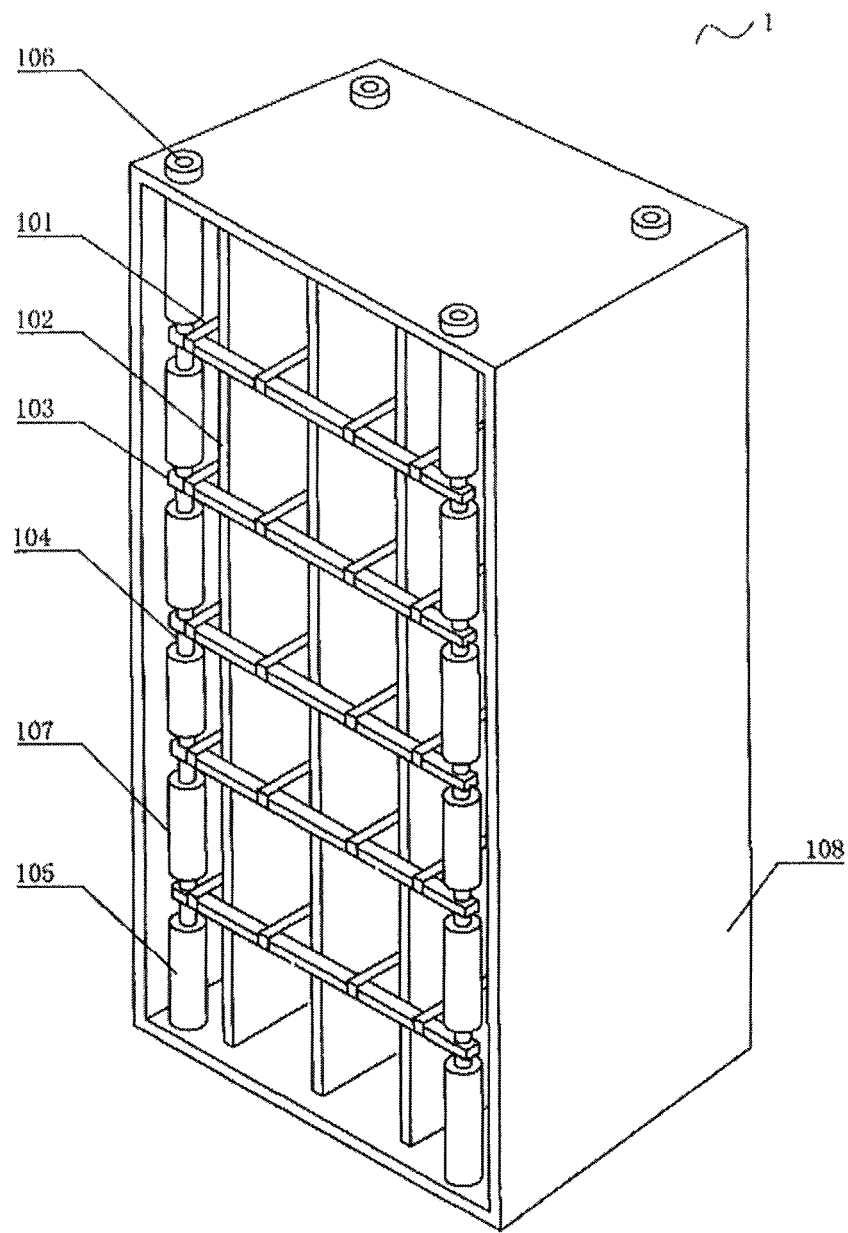
FIG. 3 is a three-dimensional view of a plasma reactor with a positive electrode made of nickel-chromium alloy belts provided by the present invention.

FIG. 1 is a structural view of a plasma air sterilizing and purifying device provided by the present invention. FIG. 2 is a three-dimensional view of a plasma reactor with a positive electrode made of nickel-chromium alloy wires provided by the present invention. FIG. 3 is a three-dimensional view of a plasma reactor with a positive electrode made of nickel-chromium alloy belts provided by the present invention. The plasma air sterilizing and purifying device provided by the present invention consists of a plasma reactor 1, a pulse power supply 2, a fan component 3, a control unit 4, an air inlet 5, an air outlet 6, a power adaptor 7 and a housing case 8; an air filter 10 is installed at the air inlet 5, an air filter 9 is installed at the air outlet 6, and the plasma reactor 1 is located in the air flow. The plasma reactor 1 has positive electrodes 101 made of several nickel-chromium alloy wires or nickel-chromium alloy belts arrayed in parallel at an equal interval on a plane, each positive electrode 101 is positioned at the middle of two adjacent negative electrodes 102. The negative electrodes 102 with a thickness of 0.8-1.5 mm are made from aluminum sheets or stainless steel sheets. The positive electrodes 101 and the negative electrodes 102 are arrayed in parallel towards the airflow direction, so the wind resistance is small and the sterilization is uniform. The two ends of the positive electrode 101 are fixed in corresponding grooves on the micro-discharge preventive conductor rail 103, and the two ends of the micro-discharge preventive conductor rail 103 are fixed at and electrically connected with four positive electrode metal supports 104 which are installed on the four sides of the reactor orthogonally. The upper and lower ends of each positive electrode metal support 104 are respectively provided with an insulation connection 105 fixed in the corresponding mounting hole on the housing 108, and the insulation connection 105 is fastened on the reactor housing 108 by an insulation terminal fixing bolt 106. The upper and lower ends of the negative electrodes 102 are directly fixed on and electrically connected with the inner wall of the metal reactor housing 108. Fixing rings 107 are installed on the edge of the positive electrode metal support 104 to isolate the micro-discharge preventive conductor rail 103 at an interval, and the lengths of the fixing rings are set to meet the requirements for reducing the mutual shielding effects of the electromagnetic fields with same polarity.

There are totally n (n is a positive integer below 30) groups of positive electrodes 101, each of which is a component formed by several nickel-chromium alloy wires or nickel-chromium alloy belts arrayed at an optimal equal interval of 24 mm on the same plane, there are totally n+1 negative electrodes 102, and the optimal distance between the positive electrode 101 and negative electrode 102 is 12 mm. The nickel-chromium alloy wires or nickel-chromium alloy belts forming the positive electrode 101 are high-resistance electrothermal alloys with a mark of Cr20Ni80; the optimal diameter of the nickel-chromium alloy wires is 0.20 mm, or the optimal width of the nickel-chromium alloy belts is 2 mm, and the thickness is 0.10 mm.

Airtight air deflectors 15 are installed at the lower parts of the air inlet 5 and the air outlet 6. The plasma reactor 1 and the air component 3 are fixed on the air deflector 15. An appliance box 11 is positioned at the lower part of the air deflector 15 for installing the pulse power supply 2 and the control unit 4. A fixing device 18 is installed on the upper part of the housing 8.

Figure 5:
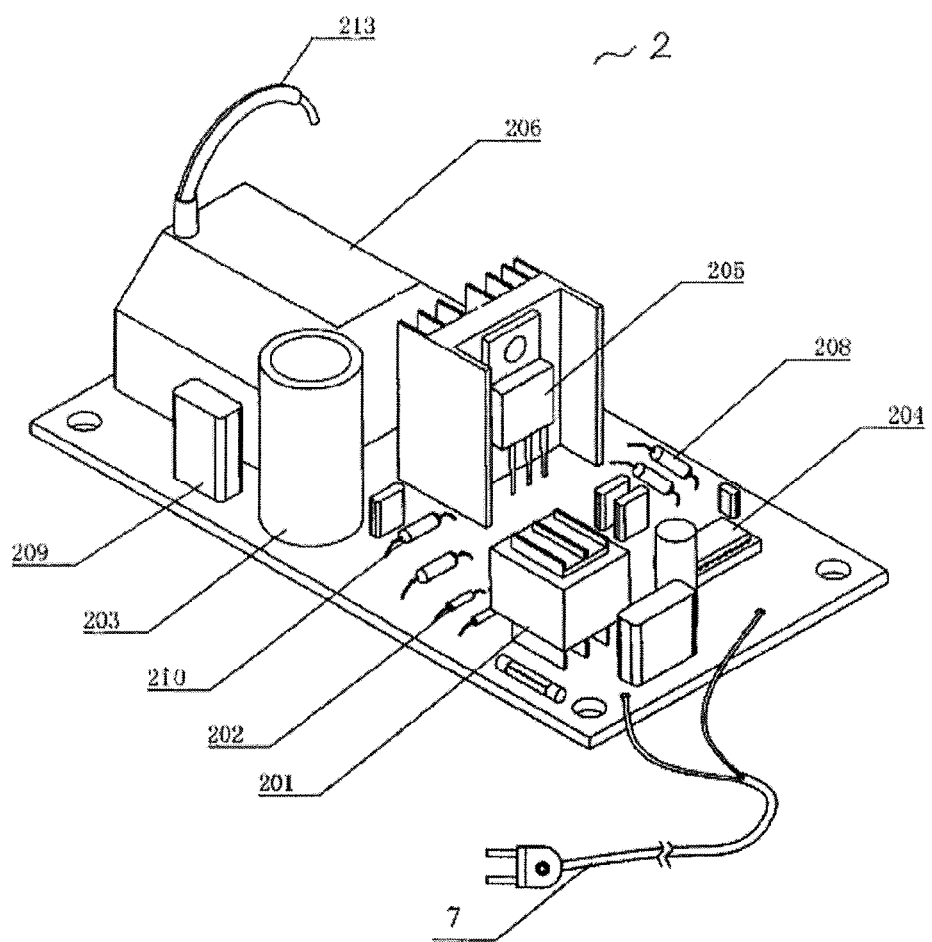
FIG. 5 is a three-dimensional view of a pulse power supply in the present invention.
Figure 6:
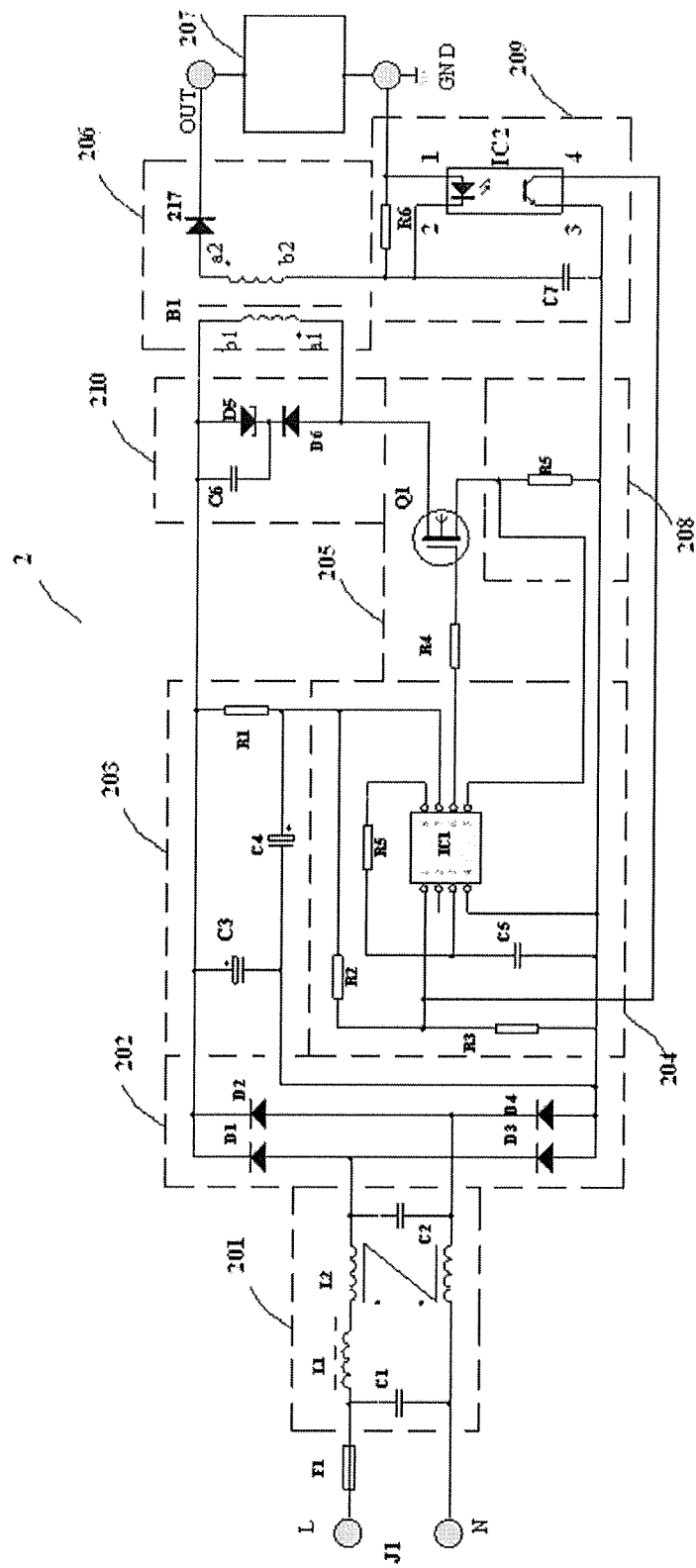
FIG. 6 is a schematic view of a pulse power supply in the present invention.

FIG. 5 is a three-dimensional view of the pulse power supply in the present invention, and FIG. 6 is a schematic view of the pulse power supply in the present invention. As shown in the figures, an EMC filter 201, a rectifier circuit 202, a filter circuit 203, a digital control circuit 204, a pulse generator 205 and a pulse transformer 206 are installed in the pulse power supply 2 and electrically connected in turn, and the positive and negative output ends of the pulse transformer 206 are respectively connected with the corresponding positive and negative electrodes of the plasma reactor 207. The output end of the pulse generator 205 is provided with a current detecting circuit 208; the detected current signal output from the pulse generator is sent to the oscillator, error amplifier and PWM comparator in the digital control circuit 204, converted into the digital control current, and then output to the input end of the pulse generator 205; then the width of the pulse output from the pulse generator 205 is adjusted automatically, and the discharge of the plasma reactor 207 is kept stable.

Figure 7:
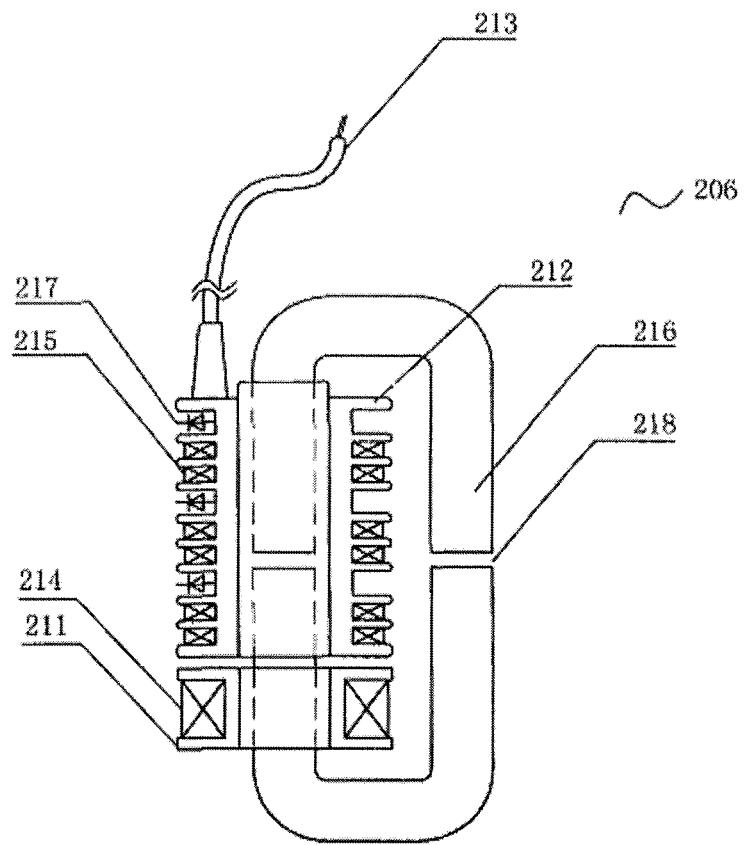
FIG. 7 is a structural view of a pulse transformer in the present invention.
Figure 8:
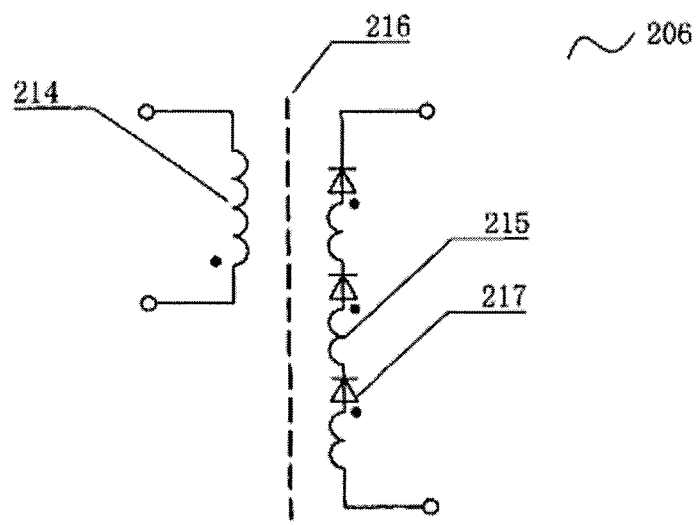
FIG. 8 is a circuit diagram of a pulse transformer in the present invention.

FIG. 7 is a structural view of the pulse transformer in the present invention, and FIG. 8 is a circuit diagram of the pulse transformer in the present invention. An insulation gate field effect transistor switch Q1 is installed in the pulse generator 205, the drain electrode is connected with the dotted terminal a1 of the primary coil 214, the grid electrode is connected with the output end of the integrated circuit IC1 in the digital control circuit 204 via a resistor R4, and the source electrode is connected with a resistor R5 in the current detecting circuit 208. The pulse generator 205 and the pulse transformer 206 are installed in accordance with the flyback inverter, while the dotted terminals a1 and a2 and unlike terminals b1 and b2 of the primary coil 214 and the secondary coil 215 of the pulse transformer 206 are installed transversely. The secondary coil 215 consists of at least two wound segments which are connected in series, and the upper end of each segment is provided with a high-voltage fast-recovery diode 217. The positive electrode of the high-voltage fast-recovery diode 217 is pressed against the tail end of the low-potential segment, and the negative electrode of the high-voltage fast-recovery diode 217 is pressed against the starting end of the high-potential segment. The high-voltage fast-recovery diode 217 performs high-frequency isolation on each segment of the secondary coil 215, and the distributed capacitance of the winding increases exponentially, which improves the speeds of the rising edge and descending edge of the output pulse and lowers the requirements for the reverse voltage resistance of the high-voltage fast-recovery diode 217. Thus, the cost reduction and the working reliability improvement, unexpected good effects, are achieved.

A filter capacitor C3 is connected with the direct current output end of the rectifier circuit 202. A voltage dropping resistor R1 is connected in series in the power supply loop of the digital control circuit 204, and a filter capacitor C4 is connected in parallel in the power supply loop of the digital control circuit 204. The oscillator loop in the digital control circuit 204 is externally connected with an oscillation resistor Rs and an oscillation capacitor Cs. The rectifier circuit 202 is connected via bridge rectifier circuit by the diodes D1, D2, D3 and D4. The L and N input ends of the non-thermal plasma pulse power supply in the present invention are provided with a power adaptor 7.

The pulse transformer 206 is provided with a multi-groove insulation coil frame 212, and the secondary coil 215 is formed by three-five segments which are wound in corresponding grooves of the multi-groove insulation coil frame 212 and connected in series. The output end of the pulse transformer 206 is provided with a high-voltage lead 213 connected with the positive electrode of the plasma reactor 207. The voltage-withstanding parameter of the high-voltage fast-recovery diode 217 is at least 12 KV, and the recovery time is less than 80 nS; the primary coil 214 is wound in the primary insulation coil frame 211, and iron-based ultra-crystalline cores 216 for electromagnetic couplings are located in the primary insulation coil frame 211 and the multi-groove insulation coil frame 212. The magnetic loops of the iron-based ultra-crystalline cores 216 have magnetic air gaps 218 with a width of 0.15-0.4 mm, which is adjusted according to the working frequency and the output power; in the optimal embodiment, the working frequency is 38 KHz, the output power is 7 W, and the magnetic air gaps 218 are 0.25 mm wide. The iron-based ultra-crystalline cores 216 may also be R2KD ferrite cores.

The working principle of the pulse power supply is as follows: When the switch Q1 in the pulse generator 205 is excited to be switched on by the PWM pulse, the secondary high-voltage fast-recovery diode 217 is switched off, and then the secondary coil 215 of the pulse transformer 206 outputs a pulse current to the external plasma rector 207. The direct current output voltage of the rectifier circuit 202 is applied to the two ends of the primary coil of the pulse transformer 206; at that moment, the primary coil 214 is equivalent to a pure inductor, the current flowing through the primary coil 214 rises linearly, and the electric energy is stored in the inductor in the form of magnetic energy; when the switch Q1 is switched off, the voltage polarities of the two ends of the primary coil 214 become reversed, because the inductive current cannot be mutational; besides, the voltage polarities of the secondary coil 215 are reversed to make the high-voltage fast-recovery diode 217 switched on, and the energy stored in the primary coil 214 is transmitted to the secondary coil 215 to supply the output pulse current to the external plasma rector 207.

The abnormal state protective circuit 209 has an optical coupler IC2, the pin 1 of the input end of the optical coupler IC2 is grounded, the pin 2 of the input end of the optical coupler IC2 is connected with the unlike terminal b2 of the secondary coil of the pulse transformer 206, the pin 3 of the output end of the optical coupler IC2 is connected with the negative output end of the rectifier circuit 202, and the pin 4 of the optical coupler IC2 is an output end. Pins 2 and 3 of the optical coupler IC2 are connected with the high-voltage capacitor C7 in parallel, and a sampling resistor R6 is connected with the input end of the optical coupler IC2 in series. The sampling current flowing through the sampling resistor R6 is sent from the pulse transformer 206 to the plasma reactor 207 during work; when the optical coupler IC2 performs optical conversion and electric isolation, the working signal current of the plasma reactor 207 is sent to the error amplifier and PWM comparator in the digital control circuit 204. An abnormal state signal current is converted into an optical signal by the optical coupler (IC2), and the optical signal is subject to photoelectric isolation and then reverted into an electric signal which is sent to the digital control circuit 204 for treatment.

The resistor R5 in the current detecting circuit 208 is the transmitter resistor of the insulation grade bipolar transistor Q1 and also the current sampling resistor of the current detecting circuit 208. The sampling current on the resistor R5 is sent to the digital control circuit 204 to be processed by the oscillator, error amplifier and PWM comparator in the digital control circuit 204, converted into a digital control current, and then sent to the input end of the pulse generator 205; then, the width of the output pulse of the pulse generator 205 is adjusted automatically, and the stability of the working current of the plasma reactor 207 is further controlled automatically.

A transient diode D5 and a fast-recovery diode D6 installed in the pulse amplitude-limiting circuit 210 are connected in series transversely and then connected with the primary coil 214 in parallel, and the positive electrode of the transient diode D5 is connected with the positive output end of the rectifier circuit 202. The positive electrode of the fast-recovery diode D6 is connected with the collector of the insulation grade bipolar transistor Q1, and the capacitor C6 is connected with the transient diode D5. The transient diode D5 plays an important role in the pulse amplitude-limiting circuit 210; in this embodiment, when the mains voltage is 220V, the preferable type is 1.5KE250A, the working current is 4.2 A, and the amplitude-limiting voltage is 237-263V.

Figure 9:
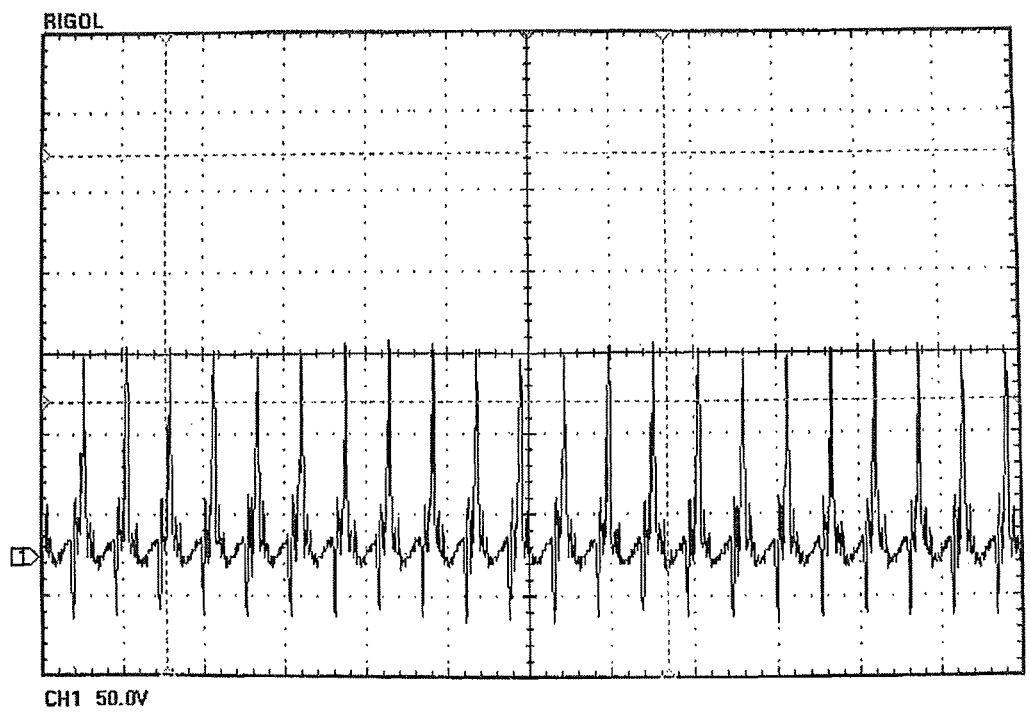
FIG. 9 is an oscillograph of a high-voltage discharge current output by a pulse transformer in the present invention.

FIG. 9 is an oscillograph of a high-voltage discharge current output by the pulse transformer in the present invention. This discharge current waveform is measured on the sampling resistor when the output end of the pulse transformer 206 is externally connected with the sampling resistor at the grounding terminal of the plasma reactor 207. The digital oscilloscope shows that the pulse duty ratio is 16%, the pulse width is 3 µS, and the pulse rise time is 70 nS. The pulse transformer outputs the high-voltage discharge current with identical waveform, and the plasma reactor 207 is stable in corona discharge.

Embodiment 2

In the plasma air sterilizing and purifying device provided by the present invention, the micro-discharge preventive conductor rail 103 is made of an aluminum rod or a stainless steel bar, and the two ends of the positive electrode 101 made of several nickel-chromium alloy wires or alloy belts are fixed and located in grooves at corresponding positions on the micro-discharge preventive conductor rail 103. Convex pins may replace the grooves to fix the nickel-chromium alloy wires, but if fixed by the convex pins, the nickel-chromium alloy belts will be inclined. The inventor tried to substitute the springs and stainless steel sheets for the grooves at the corresponding positions on the micro-discharge preventive conductor rail 103 to fix the nickel-chromium alloy wires or belts, but those experiments all failed; the most serious issue was that when the fan was started, the nickel-chromium alloy wires or belts shook fiercely because of the unstable elasticity and sparking occurred when the positive electrodes 101 were working, which inevitably influenced the stability of the plasma rector.

Embodiment 3

In a plasma air sterilizing and purifying device, the pulse transformer 206 is provided with a multi-groove insulation coil frame 212, and the secondary coil 215 is formed by three, four or five segments which are wound in the corresponding grooves of the multi-groove insulation coil frame 212 and connected in series. Generally speaking, the winding distributed capacitance of a coil divided into three segments is about ⅑ of the original, and that of a coil divided into five segments is about ¹/₂₅ of the original. Iron-based ultra-crystalline cores 216 for electromagnetic coupling are located in the primary coil 214 and secondary coil 215, the magnetic loops of the iron-based ultra-crystalline cores 216 have magnetic air gaps 218, and the distance between the magnetic air gaps 218 is adjusted according to the required output power and is 0.2-0.5 mm in this embodiment. The iron-based ultra-crystalline cores 216 may be replaced by soft ferrite magnet-cores, but the latter have low magnetic flux density and low magnetic conductivity during work and need double winding coils to obtain the same inductance value, which certainly makes the output power and pulse rise rate of the pulse transformer 206 inferior to the ultra-crystalline cores.

Embodiment 4

In the plasma air sterilizing and purifying device provided by the present invention, the fan component 3 is provided with a low-noise fan having blades with saw tooth-shaped edges, where the saw tooth height is 8 mm and the distance between the teeth is 12 mm. The fan component 3 is fixed on the housing 8 by a fan fixing plate 16, and the lower part of the fan fixing board 16 is fastened with the air deflector 15 with a fan fixing screw 17.

From the bionic viewpoint, the tips of the feathers on the edges of the bird wings are saw tooth-shaped, the noises generated by the friction between the wings fluctuate vertically, and the high-speed airflow is extremely low. The average noise coefficient of a low-noise fan having blades with saw tooth-shaped edges is 3-5 dB lower than that of a common fan with the same power and air volume. The noise of a common fan with an external diameter of 220 mm, an air tube length of 60 mm, a rated voltage of 220/50 Hz, a working current of 0.60 A and an air volume of 1,200 m³/h is 59.5 dB(A), and if the blades with the saw tooth-shaped edges are adopted, the actually measured noise is 54.8 dB(A).

Embodiment 5

In a plasma air sterilizing and purifying device provided by the present invention, a single-chip controller is installed in the control unit 4, an air quality sensor is installed at the air inlet 5, and the output end of the air quality sensor is electrically connected with the input end of the single-chip controller. A knob 12 is a manual power switch, a knob 13 is an air volume switch with maximum, medium and minimum three shifts, and a knob 14 is a control switch of working time in a scope of 1-4 hours. The output end of the control unit 4 is connected with the pulse power supply 2 and the power supply of the fan component 3. When the indoor air quality pollution exceeds the standard, the air quality sensor increases the output signals, the single-chip controller compares the signals with the set threshold value and then sends a signal current, and then the control unit 4 turns on the pulse power supply 2 and the power supply of the fan component 3 to sterilize and purify the air automatically. The single-chip controller also can set a daily automatic sterilizing and purifying program, which makes the present invention more practical.

Embodiment 6

In a plasma air sterilizing and purifying device provided by the present invention, the output ground potential end of the pulse transformer 206 is connected with an abnormal state protective circuit 209, the output end of the abnormal state protective circuit 209 is connected with the input end of the digital control circuit 204 to sample the working current sent from the pulse transformer 206 to the plasma reactor 207, the signal current undergoing the photoelectric isolation is sent to the input end of the digital control circuit 204 and the control current undergoing digital treatment from the output end of the digital control circuit 204 is sent to the input end of the pulse generator 205; then, the width of the output pulse is controlled and the working state of the pulse generator 205 is kept automatically. When the capacitive plasma reactor 207 is at an abnormal state, such as overheat, over-current, over-voltage or short circuit, the digital control circuit 204 closes the digital control current converted by the error amplifier and PWM comparator in the digital control circuit, with no pulse drive current at the output end, and therefore realizes automatic protection. The two ends of the primary coil of the pulse transformer 206 are provided with pulse amplitude-limiting circuits 210 to clamp the peak values of the output voltage at the two ends of the primary coil of the pulse transformer 206.

Embodiment 7

In a plasma air sterilizing and purifying device provided by the present invention, the EMC filter 201 has a differential-mode inductor L1 and a common-mode inductor L2 which are connected in series, the input end of the EMC filter 201 is connected with the capacitor C1 in parallel, and the output end of the EMC filter 201 is connected with the capacitor C2 in parallel.

Figure 4:
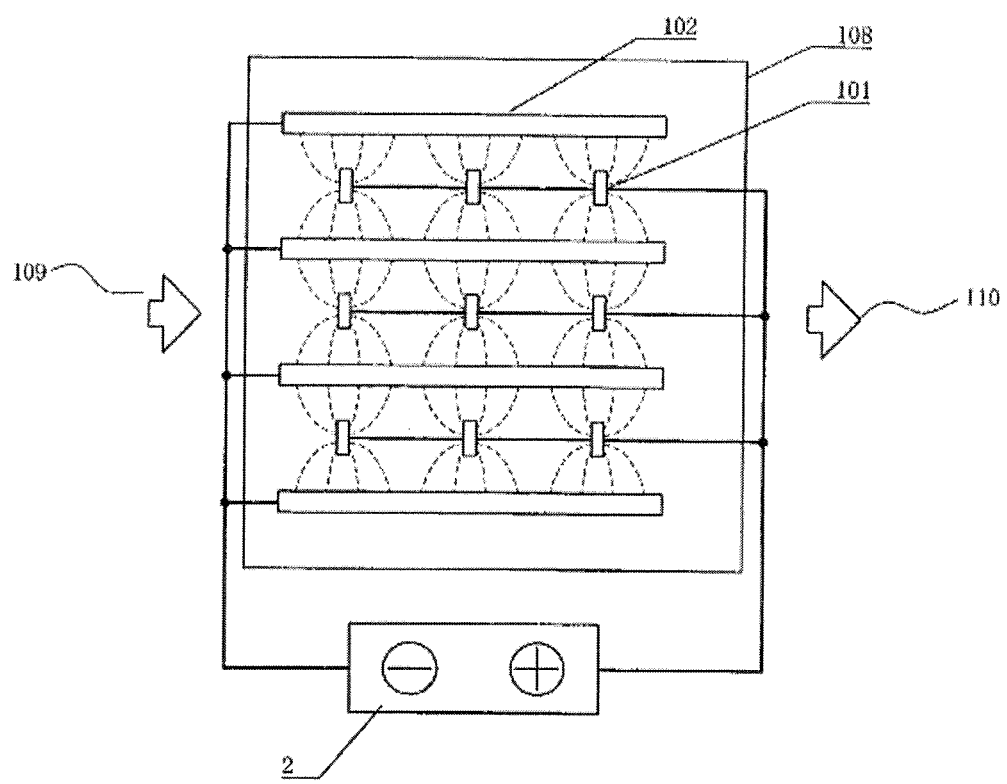
FIG. 4 is a schematic view of a plasma air sterilizing and purifying device provided by the present invention.

FIG. 4 is a schematic view of the plasma air sterilization and purification of the present invention; the polluted indoor air 109 enters the air inlet and flows through the discharge regions of the positive electrodes 101 and negative electrodes 102 from the left side, and the clean air 110 exits from the air outlet from the right side. The indoor air is driven by the fan component 3 to undergo several cycles of sterilization and purification.

The present invention provides an air sterilizing and purifying method: the indoor air flows through the positive electrode formed by several nickel-chromium alloy wires or nickel-chromium alloy belts and the micro-discharge preventive conductor rail of the plasma air sterilizing and purifying device, the pulse frequency output from the pulse power supply matched with the device ranges from 20-100 $KH_z$, the pulse width is 10-2 μS, the pulse rise time is 70-120 nS, the pulse amplitude is 12-16 $KV_{P-P}$, and the disinfection factors are non-thermal plasma. The air sterilizing and purifying method comprises the following four steps:

A. At atmospheric pressure, the indoor air is forced to flow through the plasma air sterilizing and purifying device at a speed of 0.3-0.6 m/s, by means of corona discharge the plasma air sterilizing and purifying device generates non-thermal plasma with electrons of which the temperature reaches tens of thousands of degrees centigrade, so microbes such as bacteria and viruses are unable to survive in this environment; the cells of the microbes such as bacteria and viruses are non-elastically collided by the high-energy electrons, the microbe particles bring a certain amount of charges in the electric field generated by the plasma, and then static electricity generated on the surfaces of the microbe particles breaks up the cell membranes to cause cytoplasm to flow out, so the microbes also can be killed in this way;

B. When the high-energy electrons of the plasma are collided with the molecules in the air, a series of elementary reactions occur to generate various active radicals and active oxygen, such as OH, O, $H_2O$, $H_2O_2$ and $O_3$, which decompose and reduce many kinds of organic macromolecular particular smells into harmless micro-molecular inorganic substances;

C. Fine particle contaminants with a particle size of 0.1-5 μm in the indoor air are effectively gathered by means of the condensation between the ions in the plasma and the fine particles, while fine particle contaminants with a particle size of 5-10 μm are removed by the air filter installed in the plasma air sterilizing and purifying device;

D. The flow of the indoor air passing through the plasma air sterilizing and purifying device per hour is at least 10 times the indoor air volume.

According to the air sterilizing and purifying method, the plasma generated by the corona discharge can kill microbes such as viruses and bacteria, decompose the gaseous organic contaminants and separate particles from the airflow when applied to the air sterilization and purification, and the whole process involves the pre-charge dust collection, catalytic analysis, and anion generation, etc.

Sterilizing and purifying process I: the mechanism of the pre-charge dust collection is as follows: the corona discharge is formed in an externally non-uniform electric field to generate plasma, wherein a great mount of electrons, cations and anions encounter non-elastic collision with the fine particles in the air to be attached to the surfaces of the fine particles to generate charged particles under the electric field gradient; under the action of an external electric field, the charged particles migrate towards the dust collector and are finally settled on the dust collector. This process includes three stages:

(1) e+M (gas molecules)→$M^-$;
(2) $M^-$+PM (fine particles)→(PMM);
(3) $(PMM)^-$→PMM (settled on the dust collector).

The static dust collection is a physical process which clears a part of the total suspended particles (TSP) with a diameter of less than 100 μm and respirable particles ($PM_{10}$) with a diameter of less than 10 μm suspended in the air.

Sterilizing and purifying process II: catalytic purification is based on the collision between the high-energy electrons and gas molecules. The catalytic purification mechanism includes two steps: 1, during plasma generation, high-frequency discharge occurs to generate high energy at a moment to break the chemical bonds of some harmless gas molecules and decompose the harmful molecules into elementary atoms or harmless molecules; 2, the plasma contains a great amount of active particles such as high-energy electrons, ions, excited particles and radicals with high oxidation, of which the average energy is bigger than the kinetic energy of the gas molecules; those active particles are collided with the harmful molecules frequently to break the chemical bonds of the gas molecules and generate a great amount of radicals with very strong oxidization, such as .OH, $.HO_2$, $.O^-$, and $O_3$, and the radicals and $O_3$ react with the harmful molecules to generate harmless products. The oxidizing potential (2.8 eV) of the radical .OH is 35% higher than that (2.07 eV) of ozone; therefore, the speed of the reaction between the radical .OH and the organics is several orders of magnitude higher than the reaction between ozone and organics. In the present invention, the mechanism in which that the harmful substances in the polluted air are oxidized into carbon dioxide and water or mineral substances includes the following procedures:

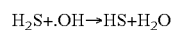

$H_2S+.OH\rightarrow HS+H_2O$

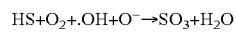

$HS+O_2+.OH+O^-\rightarrow SO_3+H_2O$

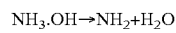

$NH_3.OH\rightarrow NH_2+H_2O$

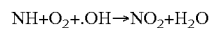

$NH+O_2+.OH\rightarrow NO_2+H_2O$

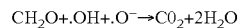

$CH_2O+.OH+.O^-\rightarrow CO_2+2H_2O$

The experiments show that the majority of the harmful substances in the polluted air can be oxidized and decomposed in a very short period of time at an average degradation rate of about 95%.

Sterilizing and purifying process III: The plasma and a great amount of anions are generated at the same time. If those anions are scattered into indoor space, on one hand the balance between the air and the ions can be adjusted, on the other hand the pollutants in the air can be cleared effectively. The high-concentration anions are collided with the harmful chemical substances and suspended virus particles in the air to bring negative charges. Those particles with negative charges absorb the nearby particles with positive charges (including bacteria, viruses, spores, etc. in the air) and become bigger. This accumulation process lasts until the particles are forced to drop to the ground due to their weight. In a natural environment, the anion concentration on the earth's surface is thousands per $cm^3$. Due to environmental pollution, the anion concentration in the city is less than $600/cm^3$. This invention can keep the concentration of anions per $cm^3$ at over five thousand. A certain concentration of anions can promote the growth and development of the human body, improve lung functions and cardiac muscle functions, increase oxygen absorption by about 20%, increase cardiac muscle nutrients and blood calcium, reduce blood sugar and cholesterol, accelerate skeleton growth, make people vigorous and energetic and sleep better and enlarge the immunologic functions of the human body.

All in all, the degradation of organics under the action of discharge is a complicated plasma chemical reaction, the radicals exist for a very short time, so the reaction speed is very quick, and a specific reaction process is very difficult to specify. Although there is much research on the pollutant degradation mechanism of non-thermal plasma, no practical theoretical system is formed yet, so the intensive research on the pollutant degradation mechanism of the non-thermal plasma is one focus of the application study.

The present invention has the following technical characteristics:

a) The present invention can sterilize the indoor air dynamically with the existence of people without injury or damage to the people and articles;

b) Various microbes in a broad spectrum are obtained from the air, and the experiments carried out in a cloud chamber prove that the destabilization efficiency reaches 99.99%;

c) The efficiency of purifying the respirable particles reaches 95%;

e) Sterilization, dust removal, particular smell removal, and organic gas elimination are carried out at the same time.

f) Anions with a concentration of up to $1 \times 10^4/cm$ can be released to make the air clear and promote the metabolism of the human body;

g) The particular noise-low fan with high air volume and high efficiency has large-volume, medium-volume and small-volume air speed options.

The present invention is applicable to the air sterilization and purification of the sites such as food factories, electronic and optical precise instrument workshops, biopharmaceutical research rooms, laboratories, hospital operating rooms and isolated wards with high requirements for clean degree and public places such as office buildings, meeting rooms, cinemas, trains, buses, subways and ships. Particularly, the H1N1 influenza A is a serious global problem, widely spreading to more than 199 countries/regions and bringing death to almost 10,000 people, so the present invention is of great significance.

The above embodiments are just further descriptions of the plasma reactor of the present invention according to the attached drawings, which shall be not regarded as limitations of the present invention. Within the technical concept of the present invention, those skilled in this field can make simple variations or equivalent substitutions for the contents, including the materials, of the micro-discharge preventive technology and pulse power supply technology of the plasma reactor, all of which belong to the scope of the technical scheme. For example, the positive electrode can be made of several nickel-chromium alloy wires or nickel-chromium alloy belts which can be equivalently replaced by prism-like, oval-shaped or triangular molybdenum or tungsten materials. But the molybdenum and tungsten materials have low mechanical strength and low oxidization resistance in air, and the prism-like, oval-shaped and triangular positive electrodes are difficult to process. The grooves for locating the micro-discharge preventive conductor rail can be replaced by metal pins or thickened elastic metal plates or springs by means of simple deformation, however the pins are difficult to screw, and the elastic metal plates and springs are susceptible to shaking during work, are unstable in discharge and have complicated manufacturing processes and increased cost. The four positive electrode metal supports can be reduced to two or one, but such structures are difficult to switch on and have poor electric contact after working for a long time. Moreover, the iron-based ultra-crystalline cores also can be replaced by soft ferrite magnet-cores. The mentioned various simple deformations or equivalent substitutions are just some examples, all belonging to the scope of the technical concept of the present invention without doubt and are variations within the spirit of the present invention and the scope defined in the claims.

What is claimed is:

1. A plasma air sterilizing and purifying device, comprising:

a plasma reactor, a pulse power supply, a fan component, a control unit, an air inlet, an air outlet, a power adaptor and a housing case, wherein a first air filter is installed at the air inlet and a second air filter is installed at the air outlet;

wherein the plasma reactor is disposed in an air flow, the plasma reactor includes positive electrodes and negative electrodes, the positive electrodes are formed by a plurality of nickel-chromium alloy wires or nickel-chromium alloy belts which are arrayed at an equal interval on the same plane, and each positive electrode is positioned at the middle between two adjacent negative electrodes; each of the positive electrodes includes two ends that are fixed on corresponding grooves on a micro-discharge preventive conductor rail, two ends of the micro-discharge preventive conductor rail are fixed to and electrically connected with four positive electrode metal supports which are installed on four sides of the plasma reactor orthogonally; upper and lower ends of each positive electrode metal support are respectively provided with an insulation connection fixed in a corresponding mounting hole on a reactor housing; upper and lower ends of the negative electrodes are directly fixed on and electrically connected with the reactor housing made of metal;

wherein the pulse power supply includes an electromagnetic compatibility (EMC) filter, a rectifier circuit, a filter circuit, a digital control circuit, a pulse generator and a pulse transformer that are installed in the pulse power supply and electrically connected in turn, and an output end of the pulse transformer (206) is externally connected with the plasma reactor; an output end of the pulse generator is provided with a current detecting circuit to send a detected current signal output from the pulse generator to an oscillator, an error amplifier and a pulse-width modulation (PMW) comparator in the digital control circuit, and the current signal output is converted into a digital control current and then sent to an input end of the pulse generator; and wherein the pulse transformer includes a primary coil and a secondary coil each having dotted terminals a1 and a2 and unlike terminals b1 and b2, the dotted terminals a1 and a2 and the unlike terminals b1 and b2 of the primary coil and the secondary coil of the pulse transformer are arranged transversely; the secondary coil is formed by at least two wound segments which are connected in series, and an upper end of each segment is provided with a high-voltage fast-recovery diode; an insulation-grade field-effect transistor (FET) switch Q1 is installed in the pulse generator, a drain electrode of the FET switch Q1 is connected with the dotted terminal a1 of the primary coil, a gate electrode of the FET switch Q1 is connected with an output end of an integrated circuit IC1 in the digital control circuit via a resistor R4, and a source electrode of the FET switch Q1 is connected with a resistor R5 in the current detecting circuit.

2. The plasma air sterilizing and purifying device according to claim 1, wherein the micro-discharge preventive conductor rail is made of an aluminum bar or a stainless steel bar, and the two ends of the positive electrodes are made of a plurality of nickel-chromium alloy wires or alloy belts and are fixed and located in grooves at corresponding positions on the micro-discharge preventive conductor rail.

3. The plasma air sterilizing and purifying device according to claim 1, wherein the pulse transformer includes a multi-groove insulation coil frame, the secondary coil is formed by three to five wound segments connected in series in corresponding grooves of the multi-groove insulation coil frame; a plurality of iron-based ultra-crystalline cores for electromagnetic coupling are located in inner holes of the primary coil and the secondary coil, and magnetic loops of the iron-based ultra-crystalline cores have magnetic air gaps.

4. The plasma air sterilizing and purifying device according to claim 1, wherein the fan component is provided with a low-noise fan having blades with saw tooth-shaped edges.

5. The plasma air sterilizing and purifying device according to claim 1, wherein the control unit has an air quality sensor and a single-chip controller, an output end of the air quality sensor is connected with an input end of the single-chip controller electrically, and an output end of the control unit is electrically connected with the switches of the pulse power supply and the fan component.

6. The plasma air sterilizing and purifying device according to claim 1, wherein an output ground potential end of the pulse transformer is connected with an abnormal state protective circuit, an output end of the abnormal state protective circuit is connected with an input end of the digital control circuit to sample a working current sent from the pulse transformer to the plasma reactor, a signal current undergoing photoelectric isolation is sent to the input end of the digital control circuit and a control current undergoing digital treatment from an output end of the digital control circuit is sent to the input end of the pulse generator, so the width of an output pulse is controlled automatically; and two ends of the primary coil of the pulse transformer are provided with pulse amplitude-limiting circuits to perform clamping on peak values of a voltage output from the two ends of the primary coil of the pulse transformer.

7. The plasma air sterilizing and purifying device according to claim 1, wherein the EMC filter has a differential-mode inductor L1 and a common-mode inductor L2 which are connected in series, an input end of the EMC filter is connected with a capacitor C1 in parallel, and an output end of the EMC filter is connected with a capacitor C2 in parallel.

8. An air sterilizing and purifying method, wherein, according to the air sterilizing and purifying method, indoor air flows through a plasma air sterilizing and purifying device which has a micro-discharge preventive conductor rail and a pulse power supply, wherein a pulse frequency is 38 $KH_Z$, a pulse width is 5 μS, a pulse rise time is 80 nS, a pulse amplitude is 16 $KV_{P-P}$, and disinfection factors are non-thermal plasma; the air sterilizing and purifying method comprising:

at an atmospheric pressure, forcing the indoor air to flow through the plasma air sterilizing and purifying device at a speed of 0.3-0.6 m/s, and generating, via a corona discharge of the plasma air sterilizing and purifying device, non-thermal plasma with high-energy electrons of which the temperature reaches 10,000° C. or above, wherein microbes including bacteria and viruses are unable to survive in the non-thermal plasma; cells of the microbes are non-elastically collided with the high-energy electrons, microbe particles bring a certain amount of charges in an electric field generated by the plasma, and static electricity generated on surfaces of the microbe particles breaks up cell membranes to cause cytoplasm to flow out, so the microbes also can be killed in this way;

colliding the high-energy electrons of the plasma with molecules in the air, and generating by a series of elementary reactors a plurality of active radicals and active oxygen, including OH, O, $H_2O$, $H_2O_2$ and $O_3$ which decompose and reduce a plurality of types of organic macromolecular gases with particular smells into harmless micro-molecular inorganic substances; and gathering fine particle contaminants with a particle size of 0.1-5 μm in the indoor air by means of the condensation between ions in the plasma and the fine particle contaminants, and removing fine particle contaminants with a particle size of 5-10 μm by an air filter installed in the plasma air sterilizing and purifying device, wherein the flow of the indoor air passing through the plasma air sterilizing and purifying device per hour is at least 10 times the indoor air volume.

* * * * *